(12) United States Patent
Shelly et al.

(10) Patent No.: US 10,342,940 B2
(45) Date of Patent: Jul. 9, 2019

(54) PRESSURE ADJUSTMENT IN A RESPIRATORY THERAPY DEVICE

(75) Inventors: Benjamin Irwin Shelly, Pittsburgh, PA (US); Michael Thomas Kane, Harrison City, PA (US); Gregory Delano Matthews, Pittsburgh, PA (US); Heather Dawn Ressler, Blairsville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 145 days.

(21) Appl. No.: 14/122,375

(22) PCT Filed: May 23, 2012

(86) PCT No.: PCT/IB2012/052583
§ 371 (c)(1),
(2), (4) Date: Nov. 26, 2013

(87) PCT Pub. No.: WO2012/164445
PCT Pub. Date: Dec. 6, 2012

(65) Prior Publication Data
US 2014/0109909 A1    Apr. 24, 2014

Related U.S. Application Data

(60) Provisional application No. 61/493,065, filed on Jun. 3, 2011.

(51) Int. Cl.
*A61M 16/00* (2006.01)
*A61M 16/16* (2006.01)
(Continued)

(52) U.S. Cl.
CPC .... *A61M 16/0051* (2013.01); *A61M 16/0066* (2013.01); *A61M 16/0069* (2014.02);
(Continued)

(58) Field of Classification Search
CPC .......... A61M 16/0051; A61M 16/0875; A61M 16/0066; A61M 16/06; A61M 16/161;
(Continued)

(56) References Cited

U.S. PATENT DOCUMENTS 7,469,698 B1    12/2008  Childers
8,314,546 B2    11/2012  Tchakarov
(Continued)

FOREIGN PATENT DOCUMENTS

JP    2006516442 A    7/2006
WO   WO0067827 A1   11/2000
(Continued)

*Primary Examiner* — Gregory A Anderson
*Assistant Examiner* — Margaret M Luarca
(74) *Attorney, Agent, or Firm* — Michael W. Haas

(57) ABSTRACT

Sleep apnea can be treated with pressure support therapy using a target pressure level. Detected respiratory events during consecutive multi-session testing period are compared to determine statistical metrics covering gradual changes in therapy efficiency. Adjustments to the target pressure level are based on changes in variability, and maybe made in between therapy sessions.

24 Claims, 4 Drawing Sheets

(51) Int. Cl.
*A61M 16/06* (2006.01)
*A61M 16/08* (2006.01)

(52) U.S. Cl.
CPC .......... *A61M 16/024* (2017.08); *A61M 16/06* (2013.01); *A61M 16/0875* (2013.01); *A61M 16/161* (2014.02); *A61M 2016/0027* (2013.01); *A61M 2016/0036* (2013.01); *A61M 2205/52* (2013.01)

(58) Field of Classification Search
CPC ...... A61M 16/0069; A61M 2016/0036; A61M 2016/0027; A61M 2205/52
USPC .................................................... 128/204.23
See application file for complete search history.

(56) References Cited

U.S. PATENT DOCUMENTS

| | | | |
|---|---|---|---|
| 2003/0111079 A1* | 6/2003 | Matthews | A61M 16/0051 128/204.18 |
| 2005/0241639 A1* | 11/2005 | Zilberg | A61B 5/0803 128/204.21 |
| 2006/0070625 A1* | 4/2006 | Ayappa | A61M 16/0051 128/204.23 |
| 2007/0043306 A1 | 2/2007 | Olson | |
| 2007/0095349 A1 | 5/2007 | Hansmann | |
| 2008/0043440 A1 | 3/2008 | Farrugia | |
| 2008/0060647 A1* | 3/2008 | Messenger | A61M 16/024 128/204.23 |
| 2008/0078384 A1* | 4/2008 | Messenger | A61M 16/0051 128/203.12 |
| 2009/0038616 A1 | 2/2009 | Mulcahy | |
| 2010/0024811 A1 | 2/2010 | Henry | |

FOREIGN PATENT DOCUMENTS

| | | |
|---|---|---|
| WO | WO0074755 A1 | 12/2000 |
| WO | WO2005077447 A1 | 8/2005 |
| WO | WO2008037020 A1 | 4/2008 |
| WO | WO2011003128 A1 | 1/2011 |

* cited by examiner

PRESSURE ADJUSTMENT IN A RESPIRATORY THERAPY DEVICE

CROSS-REFERENCE TO RELATED APPLICATIONS

This patent application claims the priority benefit under 35 U.S.C. § 371 of international patent application no. PCT/IB2012/052583, filed May 23, 2012, which claims the priority benefit under 35 U.S.C. § 119(e) of U.S. Provisional Application No. 61/493,065 filed on Jun. 3, 2011, the contents of which are herein incorporated by reference.

BACKGROUND OF THE INVENTION

1. Field of the Invention

The present disclosure pertains to systems and methods for treating sleep apnea, and, in particular, treating obstructive sleep apnea in an automated fashion with positive airway pressure support.

2. Description of the Related Art

It is well known to treat sleep apnea with a respiratory therapy, in particular traditional constant positive airway pressure (CPAP) therapies. Under certain circumstances, e.g. when the requirements of a patient using CPAP change gradually, it may be beneficial to use a mode of CPAP therapy in which the pressure level can also be adjusted gradually.

SUMMARY OF THE INVENTION

Accordingly, it is an object of one or more embodiments of the present disclosure to provide a system for treating sleep apnea of a subject having an airway by adjusting a pressure level. The system includes a pressure generator, one or more sensors, a respiratory event module, a target pressure module, and a control module. The pressure generator is configured to generate a pressurized flow of breathable gas for delivery to the airway of the subject, in accordance with a therapeutic regimen. The one or more sensors are configured to generated output signals conveying measurements related to the pressurized flow of breathable gas and/or the airway of the subject. The respiratory event module is configured to detect respiratory events based on the generated output signals. The target pressure module is configured to adjust a target pressure level based on the detected respiratory events, such that consecutive adjustments occur at least a threshold amount of usage apart, wherein the threshold amount of time corresponds to therapeutic usage spanning more than one therapy session.

It is yet another aspect of one or more embodiments of the present disclosure to provide a method of treating sleep apnea of a subject having an airway by adjusting a pressure level. The method comprises delivering a pressurized flow of breathable gas having a pressure level at or near a target pressure level to the airway of a subject; generating one or more output signals conveying measurements related to the pressurized flow of breathable gas and/or the airway of the subject; detecting respiratory events based on the generated output signals; and adjusting the target pressure level based on the detected respiratory events, such that consecutive adjustments occur at least a threshold amount of usage apart, wherein the threshold amount of usage corresponds to therapeutic usage spanning more than one therapy session.

It is yet another aspect of one or more embodiments to provide a system configured to treat (obstructive) sleep apnea of a subject having an airway by adjusting a pressure level. The system comprises means for delivering a pressurized flow of breathable gas having a pressure level at or near a target pressure level to the airway of a subject; means for generating one or more output signals conveying measurements related to the pressurized flow of breathable gas and/or the airway of the subject; means for detecting respiratory events based on the generated output signals; and means for adjusting the target pressure level based on the detected respiratory events, such that consecutive adjustments occur at least a threshold amount of usage apart, wherein the threshold amount of usage corresponds to therapeutic usage spanning more than one therapy session.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
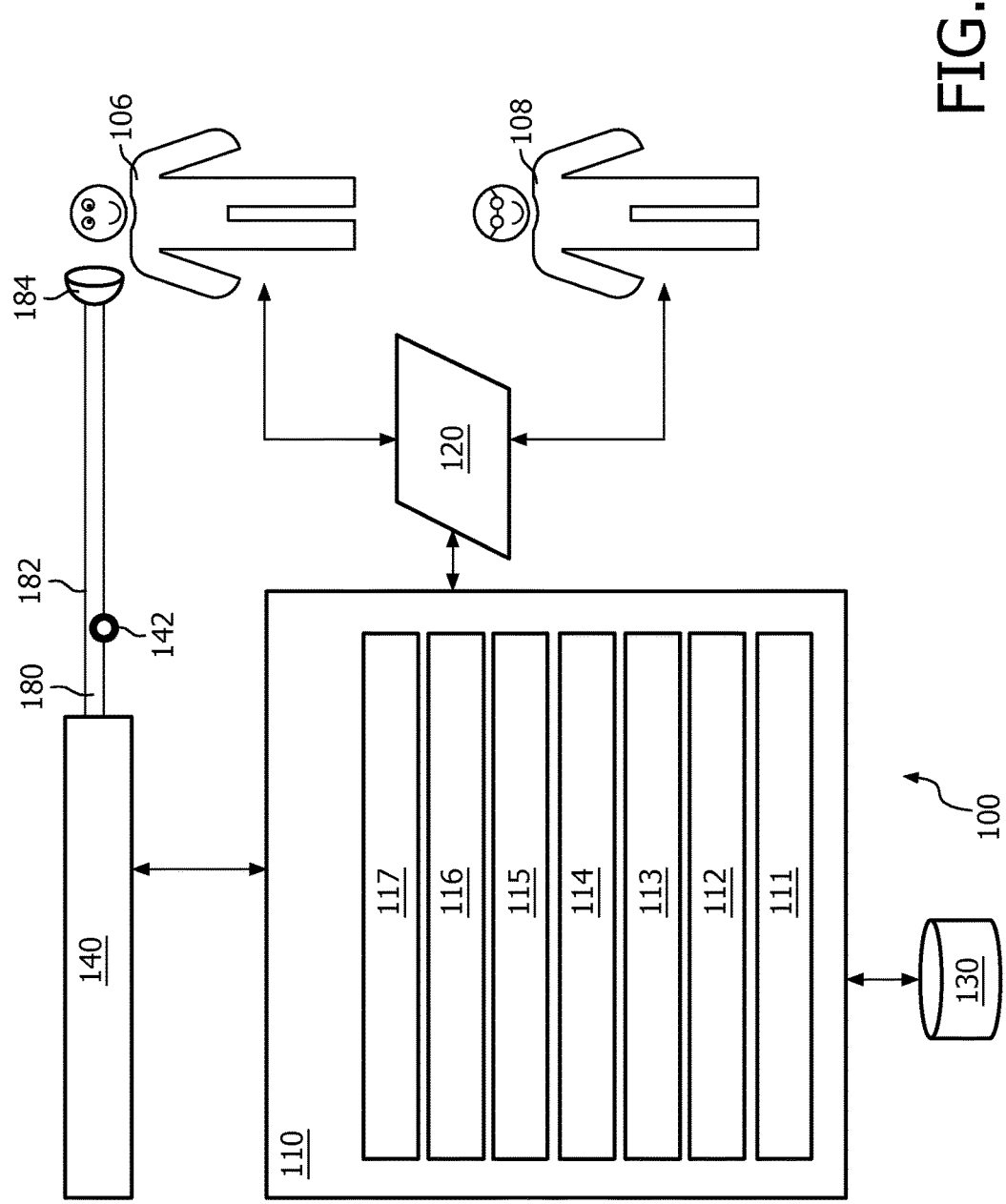
FIG. 1 schematically illustrates a system configured to treat sleep apnea by adjusting a pressure level, according to certain embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to treat sleep apnea by adjusting a pressure level, according to certain embodiments. System 100 may be implemented as a respiratory therapy device. A therapy "session" of using the system may be defined as a period of substantially uninterrupted therapeutic usage of the system, not to exceed some upper threshold of (consecutive) hours. The upper threshold may be, for example, about 10 hours, about 12 hours, about 16 hours, about 24 hours and/or other time periods. If the respiratory therapy is used to treat sleeping disorders the related session length may correspond to the sleeping pattern of a subject. A typical session length may thus be about eight hours.

In some modes of respiratory therapy, one or more pressure levels are adjusted on a relatively ongoing manner (e.g., each breath, every few breaths, every few seconds, etc.) during an individual therapy session to titrate the therapy. In other modes of therapy, particularly those of interest to the present disclosure, adjustments may be made more intermittently and/or only between sessions rather than during sessions. For modes in which one or more pressure levels are not adjusted on a relatively ongoing basis, setting upper and lower thresholds of a respiratory event index, and adjusting the pressure level accordingly, may result in undesirable respiratory treatment.

System 100 may include one or more of a pressure generator 140, a subject interface 180, one or more sensors 142, an electronic storage 130, a user interface 120, a processor 110, a parameter determination module 111, a respiratory event module 112, a timing module 113, a statistical module 114, a voting module 115, a target pressure module 116, a control module 117, and/or other components.

Pressure generator 140 may be integrated, combined, or connected with a (positive) airway pressure device (PAP/CPAP/BiPAP®/etc.) and configured to provide a pressurized flow of breathable gas for delivery to the airway of subject 106, e.g. via subject interface 180. Subject 106 may or may not initiate one or more phases of respiration. Pressure support may be implemented as a higher and lower positive pressure of a (multi-level) PAP device. For example, to support inspiration, the pressure of the pressurized flow of breathable gas may be adjusted to an Inspiratory Positive Airway Pressure (IPAP). Alternatively, and/or simultaneously, to support expiration, the pressure of the pressurized flow of breathable gas may be adjusted to an Expiratory Positive Airway Pressure (EPAP). Other schemes for providing respiratory support through the delivery of the pressurized flow of breathable gas are contemplated. Pressure generator 140 may be configured to adjust pressure levels, flow, humidity, velocity, acceleration, and/or other parameters of the pressurized flow of breathable gas in substantial synchronization with the breathing cycle of the subject, e.g. when the subject is sleeping. In certain embodiments, pressure generator 140 is part of an airway pressure device configured to provide types of therapy other than positive airway support therapy.

A pressurized flow of breathable gas may be delivered from pressure generator 140 to the airway of subject 106 by a subject interface 180. Subject interface 180 may include a conduit 182 and/or a subject interface appliance 184. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 may be configured to deliver the pressurized flow of breathable gas to or near the airway of subject 106. As such, subject interface appliance 184 may include any appliance suitable for this function. In one embodiment, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Electronic storage 130 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more (breathing) parameters (as discussed elsewhere herein), information indicating whether the subject adequately complied with a therapy regimen, information indicating whether and/or when a respiratory event occurred, and/or other information. Electronic storage 130 may be a separate component within system 100, or electronic storage 130 may be provided integrally with one or more other components of system 100 (e.g., processor 110).

User interface 120 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to subject 106 is a report detailing the changes in pressure levels throughout a period during which the subject is sleeping. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to subject 106 by user interface 120 in the form of auditory signals, visual signals, tactile signals, and/or other sensory signals.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to subject 106 information related to breathing and/or the pressurized flow of breathable gas. Note that the subject and the user of system 100 may be one and the same person.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize the implementation of system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

Sensor 142 may be configured to generate output signals conveying measurements related to parameters of respiratory airflow or airway mechanics. These parameters may include one or more of flow, pressure, humidity, velocity, acceleration, and/or other parameters. Sensor 142 may be in fluid communication with conduit 182 and/or subject interface appliance 184.

The illustration of sensor 142 including a single member in FIG. 1 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as rotor speed, motor speed, blower speed, fan speed, or a related measurement that may serve as a proxy for any of the previously listed parameters through a previously known and/or calibrated mathematical relationship. Resulting signals or information from sensor 142 may be transmitted to processor 110, user interface 120, electronic storage 130, and/or other components of system 100. This transmission can be wired and/or wireless.

Processor 110 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 includes a plurality of processing units.

As is shown in FIG. 1, processor 110 is configured to execute one or more computer program modules. The one or more computer program modules include one or more of a parameter determination module 111, a respiratory event module 112, a timing module 113, a statistical module 114, a voting module 115, a target pressure module 116, a control module 117, and/or other modules. Processor 110 may be configured to execute modules 111, 112, 113, 114, 115, 116, and/or 117 by software; hardware; firmware; some combination of software, hardware, and/or firmware; and/or other mechanisms for configuring processing capabilities on processor 110.

It should be appreciated that although modules 111, 112, 113, 114, 115, 116, and 117 are illustrated in FIG. 1 as being co-located within a single processing unit, in implementations in which processor 110 includes multiple processing units, one or more of modules 111, 112, 113, 114, 115, 116, and/or 117 may be located remotely from the other modules. The description of the functionality provided by the different modules 111, 112, 113, 114, 115, 116, and/or 117 described below is for illustrative purposes, and is not intended to be limiting, as any of modules 111, 112, 113, 114, 115, 116, and/or 117 may provide more or less functionality than is described. For example, one or more of modules 111, 112, 113, 114, 115, 116, and/or 117 may be eliminated, and some or all of its functionality may be provided by other ones of modules 111, 112, 113, 114, 115, 116, and/or 117. Note that processor 110 may be configured to execute one or more additional modules that may perform some or all of the functionality attributed below to one of modules 111, 112, 113, 114, 115, 116, and/or 117.

Parameter determination module 111 is configured to determine one or more gas parameters, breathing parameters, and/or other parameters from the output signals generated by sensor(s) 142. The one or more gas parameters may be related to and/or derived from measurements of one or more of (peak) flow, flow rate, (tidal) volume, pressure, temperature, humidity, velocity, acceleration, gas composition (e.g. concentration(s) of one or more constituents), thermal energy dissipated, (intentional) gas leak, and/or other measurements related to the (pressurized) flow of breathable gas. The one or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, and/or other breathing parameters. Some or all of the stated functionality of parameter determination module 111 may be incorporated or integrated into other computer program modules of processor 110.

Timing module 113 is configured to determine respiratory timing parameters and/or other timing parameters related to the operation of system 100. Respiratory timing parameters may include transitional moments that separate inhalation phases from exhalation phases and vice versa, breathing period, respiratory rate, inhalation time or period, exhalation time or period, and/or other respiratory timing parameters. Timing parameters related to the operation of system 100 may include therapy session length, average and/or cumulative daily and/or nightly usage, amount of usage since the most recent pressure adjustment, and/or other timing parameters related to the operation of system 100.

Respiratory event module 112 is configured to detect occurrences of respiratory events, e.g. based on output signals generated by sensor 142. Respiratory event module 112 may be configured to detect occurrences of respiratory events based on parameters determined by parameter determination module 111. For example, respiratory event module 112 may detect occurrences of Cheyne-Stokes respiration, central apneas, obstructive apneas, hypopneas, snoring, hyperventilation, arousals, and/or other respiratory events. Note that functionality attributed to respiratory event module 112 may be incorporated by one or more other components of system 100.

Statistical module 114 is configured to determine a statistical metric based on one or more of output signals generated by sensor 142, parameters determined by parameter determination module 111, respiratory events detected by respiratory event module 112, (respiratory) timing parameters determined by timing module 113, and/or other components of system 100. Various statistical operations may be performed by statistical module 114, including, but not limited to, standard deviation, mean value, and average. Statistical module 114 may be configured to determine the variability for one or more detected occurrences of respiratory events. Statistical metrics may be related to a specific duration of time and/or usage, e.g. an hour, a day, a week, 30 hours, two weeks, four weeks, a month, and/or other durations of time and/or usage. Such durations—as used to determine statistical metrics—may be user-configurable and/or user-programmable. Statistical module 114 may use signals and/or information from timing module 113 to determine durations of time and/or usage.

Statistical module 114 may aggregate signals and/or information from respiratory module 112, pertaining to respiratory events, to determine an index and/or a statistical metric associated with an index. In some embodiments, an index of events could be the number of events that occurred during a particular measurement period, and/or any measure derived therefrom. Examples of indices include an apnea-hypopnea index (AHI), an obstructive apnea-hypopnea index, respiratory disturbance index (RDI), respiratory effort related arousal (RERA) index, obstructive respiratory disturbance index (ORDI), snore index, and/or any combination thereof. For example, the ORDI may include obstructive apneas, hypopneas, and RERAs for a predetermined measurement period. Experimental testing data supports the theory that subjects suffering a higher index of respiratory events may experience more variability in occurrences of respiratory events.

For the purpose of illustrating the operation of statistical module 114, an exemplary index may be the ORDI, which may be determined by respiratory event module 112. It will be appreciated that this is not intended to be limiting, and the function described herein with respect to ORDI could be accomplished with one or more other metrics and/or indices determined by statistical module 114. Statistical module 114 may be configured to determine the mean value and/or standard deviation of the ORDI for particular testing periods. A testing period may be, for example, a usage period spanning 30 hours of therapeutic usage of system 100 by subject 106. Statistical module 114 may further be configured to determine the mean value and/or standard deviation for a plurality of sub-periods of a (30-hour) testing period. For example, a testing period may include six sub-periods spanning five hours of therapeutic usage each. By comparing the mean values and/or standard deviations across different testing periods, the statistical metrics determined by statistical module 114 may indicate whether a subject suffering from sleep disorders, in particular sleep apnea, is improving, declining, or neither. Note that functionality attributed to statistical module 114 may be incorporated by one or more other components of system 100. The given examples are not meant to be limiting. Testing periods and sub-periods may have different values than the stated examples, and/or be determined depending on a different basis.

Voting module 115 is configured to determine two or more independently determined votes that a subject is improving, declining, or neither. As used herein, a "vote" is an indication of the medical state and/or medical condition of the subject, related to respiratory disorders in general, and to occurrences of respiratory disturbances in particular. Different schemes to determine a vote are contemplated. By attributing a numerical value to a vote, multiple votes may be aggregated arithmetically. For example, a vote that a subject is improving may be represented by +1 (plus one), thus incrementing the combined (additive) vote by one. A vote that a subject is declining may be represented by −1 (minus one), thus decrementing the combined (additive) vote by one. A vote may indicate that a subject is neither improving nor declining. Two opposite votes may, in this example, negate each other. It will be appreciated that these three potential vote types is not intended to be limiting. Vote types may include additional graduations to indicate relatively large improvement (e.g., +2), relatively large declines (e.g., −2), and/or other graduations.

In some implementations, votes may be combined by multiplication and/or other arithmetic operations. Multiple votes may be combined to determine if the current respiratory therapy should be adjusted. Voting module 115 is configured to determine (i) a first vote based on a comparison of detected respiratory events (and/or statistical metrics based thereon) during a first set of therapy sessions (e.g. the current testing period) and detected respiratory events (and/or statistical metrics based thereon) during a second set of therapy sessions (e.g. the previous testing period), and (ii) a second vote based on a comparison of detected respiratory events (and/or statistical metrics based thereon) during the first set of therapy sessions and detected respiratory events (and/or statistical metrics based thereon) during a third set of therapy sessions (e.g. the testing period prior to the previous testing period). One or more therapy sessions of the second set may precede the therapy sessions of the first set, and one or more therapy sessions of the third set may precede the therapy sessions of the second set. In some embodiments, the second set of therapy sessions precedes the first set of therapy sessions without overlap, and the third set of therapy sessions comprises the second set of therapy sessions, as well as earlier therapy sessions.

Figure 4:
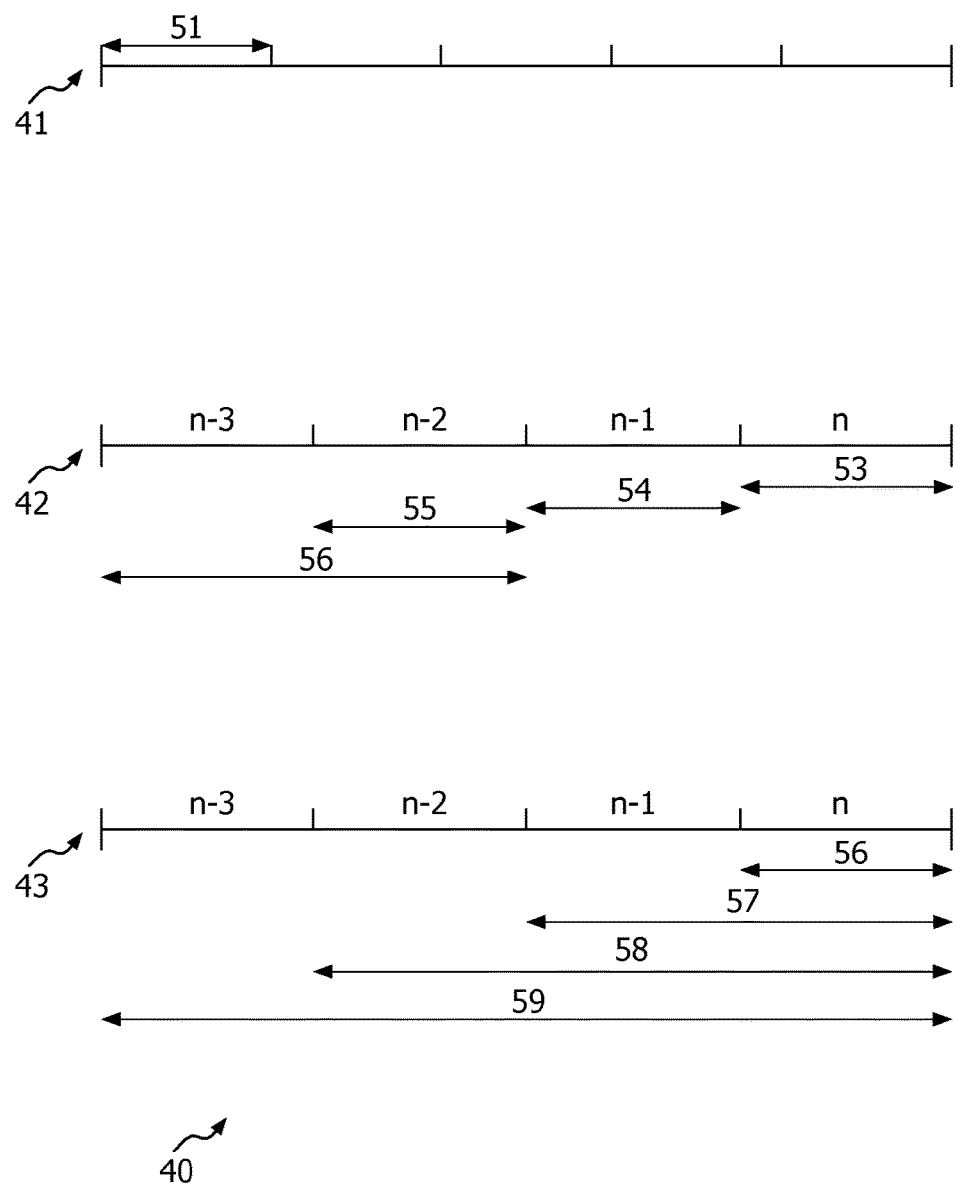
FIG. 4 illustrates (sets of) exemplary testing periods.

By way of illustration, FIG. 4 illustrates (sets of) exemplary testing periods 40. Testing period 41 denotes a single testing period spanning, e.g., 30 hours of therapeutic usage of a respiratory therapy device. The duration of a testing period is not intended to be limited to this example. A testing period may include multiple therapy sessions. As shown, testing period 41 may be divided into multiple sub-periods 51, which may or may not be of equal length/duration. A single therapy session may partially fall in two consecutive sub-periods, or even in two consecutive testing periods. In the example shown, sub-period 51 spans 6 hours of therapeutic usage, such that 5 consecutive sub-periods together form testing period 41. The number of sub-periods is not intended to be limited to this example.

Set 42 of testing periods in FIG. 4 illustrates four consecutive testing periods, which may or may not be of equal length/duration. The four testing periods are labeled "n", "n−1", "n−2", and "n−3". Testing period n of set 42 may represent the current testing period. Testing period n−1 of set 42 may represent the previous testing period which may or may not immediately precede the current testing period. Similarly, testing period n−2 may precede testing period n−1, and testing period n−3 may precede testing period n−2. Voting module 115 may use set 42 of testing periods as follows: a first set of therapy sessions 53 may coincide with the current testing period. A second set of therapy sessions 54 may coincide with the previous testing period. A third set of therapy sessions 55 may coincide with testing period n−2. Alternatively, a set of therapy sessions 56 may be used by voting module 115, coinciding with both testing period n−2 and n−3. In some embodiments, the first, second, and/or third set of therapy sessions have no overlap, as shown in set 42 of testing periods.

Set 43 of testing periods in FIG. 4 illustrates four consecutive testing periods, which may or may not be of equal length/duration. The four testing periods are labeled "n", "n−1", "n−2", and "n−3". Testing period n of set 43 may represent the current testing period. Testing period n−1 of set 43 may represent the previous testing period which may or may not immediately precede the current testing period. Similarly, testing period n−2 may precede testing period n−1, and testing period n−3 may precede testing period n−2. Voting module 115 may use set 43 of testing periods as follows: a first set of therapy sessions 56 may coincide with the current testing period. A second set of therapy sessions 57 may coincide with both the current testing period and the previous testing period. A third set of therapy sessions 58 may coincide with testing periods n, n−1, and n−2. A fourth set of testing sessions may coincide with all four testing periods. In some embodiments, the first, second, third, and/or fourth set of therapy sessions have overlap, as shown in set 43 of testing periods. Note that voting module 115 may determine one or more votes based on comparing detected respiratory events during two sets of therapy sessions spanning different lengths/durations.

For example, for the first vote voting module 115 may compare a current testing period (using indicator n) with the previous testing period (using indicator n−1). The subject receives a vote for improving if $ORDI(n) < ORDI(n-1) - \sigma_{min}$, wherein $\sigma_{min}$ is the minimum value for a measure of variability, e.g. standard deviation, in either the current or previous testing period. Alternatively, the subject also receives a vote for improving if both $$\sigma(n) < \frac{\sigma(n-1)}{2}$$

and $ORDI(n) < ORDI(n-1) - 1$

Note that σ(n) and σ(n−1) may represent measures of variability (of detected respiratory events) for the current and previous testing period, respectively. Conversely, the subject receives a vote for declining if $ORDI(n) > ORDI(n-1) + \sigma_{min}$ Alternatively, the subject also receives a vote for declining if both $\sigma(n) > 2*\sigma(n-1)$ and $ORDI(n) > ORDI(n-1) + 1$ Determination of the second vote is similar to the first vote, but uses the testing period prior to the previous testing period (using indicator n−2). In some embodiments, voting module 115 compare multiple testing periods prior to the current testing period to determine a second vote.

Voting module 115 may be configured to determine a third vote based on a comparison of detected respiratory events during the first set of therapy sessions and detected respiratory events during a fourth set of therapy sessions. In some implementations, the third vote corresponds to a long-term indication, e.g. long-term average, indicating the condition of the subject over a period spanning significant therapeutic usage. For example, in some implementations, to determine a long-term average the system may use a IIR lowpass filter. One or more therapy sessions of the fourth set precede the therapy sessions of the first set, and the therapy sessions of the fourth set span at least twice as much amount of usage as the therapy sessions of the first set. The multiple votes may then be added to determine if the current respiratory therapy should be adjusted, e.g. by increasing the pressure level (i.e. to counteract the decline of the condition of a subject), or by decreasing the pressure level (e.g. to support an improving condition of a subject while easing the respiratory therapy). Alternatively, and/or simultaneously, the pressure level may be maintained to support an improving condition of a subject, and/or decreased when the condition of a subject has neither significantly improved nor declined for at least a predetermined minimum number of testing periods.

Target pressure module 116 is configured to adjust a target pressure level based on the generated output values, determine parameters, detected respiratory events, determined statistical metrics, and/or determined votes. For example, in an embodiment using two votes, target pressure module 116 may be configured to only adjust the target pressure level if both votes agree. Other schemes are contemplated. In an embodiment using three votes, target pressure module 116 may be configured to only adjust the target pressure level if at least two votes agree, or by adding the votes together, or through another scheme. The amount of the adjustment may be predicated on agreement between the votes and/or other factors.

The target pressure level may be adjusted such that consecutive adjustments occur at least a threshold amount of usage apart. The threshold amount of usage may correspond to a period spanning more than one therapy session. The threshold amount of usage may be one hour, eight hours, 10 hours, 20 hours, 30 hours, 40 hours, a number of hours corresponding to five days of therapeutic usage, one week of therapeutic usage, 10 days of therapeutic usage, two weeks of therapeutic usage, and/or another threshold amount of usage. Target pressure module 16 may optionally be configured to adjust the pressure level in between therapy sessions and/or testing periods, rather than during therapy sessions and/or testing periods, respectively. Target pressure module 16 may be configured to adjust the pressure level after at least a threshold number of therapy sessions (optionally having a minimum therapy session length in order to be counted towards the threshold number of therapy sessions) have occurred since the previous adjustment (or since initialization of system 100).

In some embodiments, target pressure module 116 is configured to periodically adjust the target pressure level upwards or downwards, tentatively. Such a tentative adjustment may occur, for example, responsive to a determination that a certain number of testing periods have elapsed without any adjustment of the target pressure level. Based on the response by the subject to the new pressure level—as evidenced through statistical measures and/or votes determined by voting module 115—the tentative adjustment may be accepted or reverted. Tentative adjustments may alternate between upwards adjustments and downwards adjustments in a continual and proactive search for a lower index of respiratory disturbance.

Control module 117 is configured to control pressure generator 140 in the provision of a pressurized flow of breathable gas delivered to the airway of subject 106 at or near a target pressure level. The target pressure level may be provided by target pressure module 116. Control module 117 may control aspects and/or settings of pressure generator 140 in order to adjust one or more parameters of the respiration of subject 106, particularly pressure level at or near the airway of subject 106. Application of the target pressure level is intended to support the airway of subject 106. This may include preventing a collapsed and/or obstructed airway of subject 106.

Figure 2:
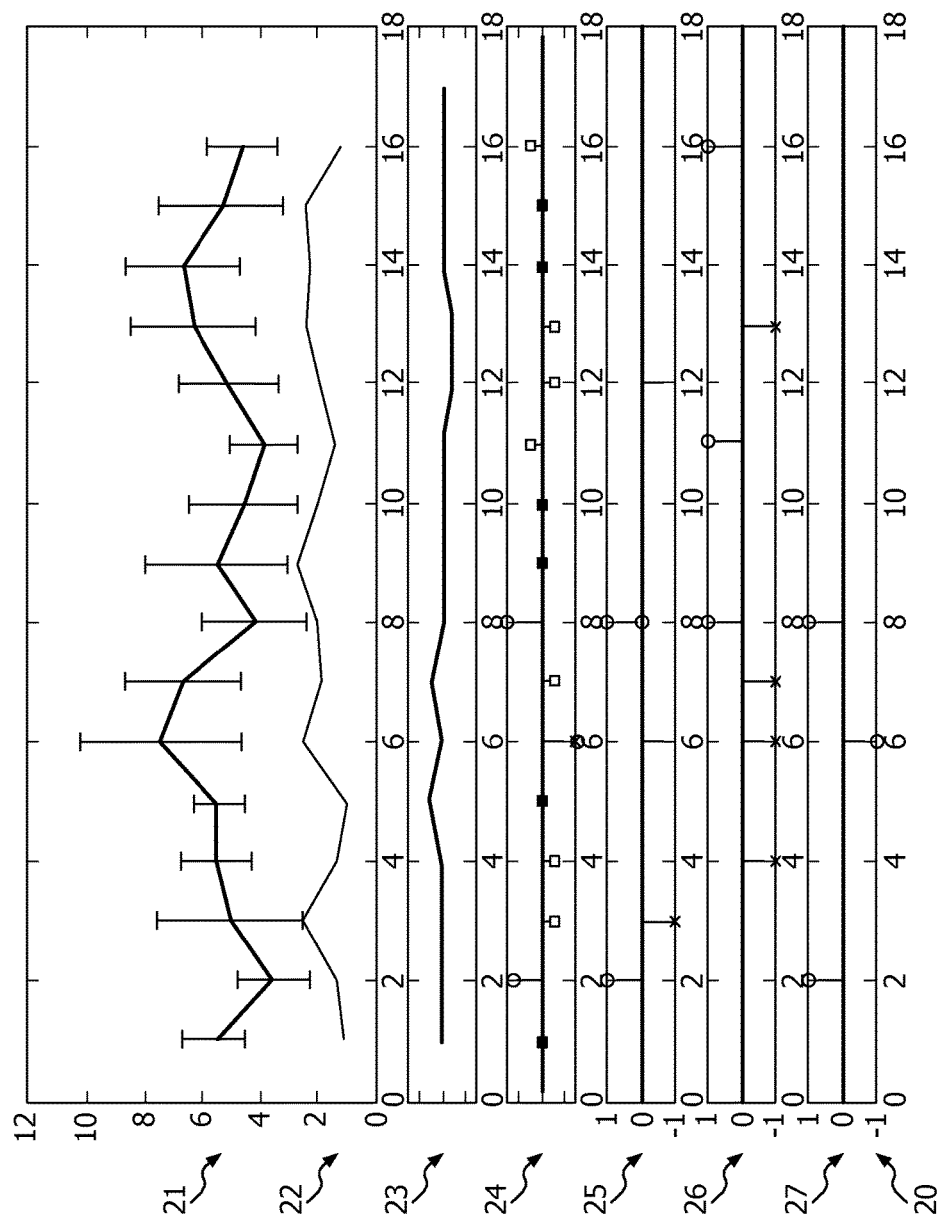
FIG. 2 illustrates vote calculation in accordance with one or more embodiments.

By way of illustration, FIG. 2 illustrates vote calculation in accordance with one or more embodiments. Set of diagrams 20 illustrate common consecutive testing periods on their X-axes, labeled from 0 to 18. Mean diagram 21 illustrates the mean ORDI value for testing periods 1 through 16. The error-bars in mean diagram 21 illustrate the standard deviation per testing period, as does standard deviation diagram 22. First vote diagram 25 illustrates the value of the first vote as determined by voting module 115 per testing period. Therefore, the Y-axis for first vote diagram 25 ranges from −1 to +1.

For example, at testing period 6, the first vote is −1. Second vote diagram 26 illustrates the value of the second vote as determined by voting module 115 per testing period. Likewise, the Y-axis for second vote diagram 26 ranges from −1 to +1. For example, at testing period 8, the second vote is +1. Third vote diagram 27 illustrates the value of the third vote (a.k.a long-term vote) as determined by voting module 115 per testing period. Likewise, the Y-axis for third vote diagram 27 ranges from −1 to +1. Combined vote diagram 24 illustrates the combination/addition of first, second, and third vote per testing period. Therefore, the Y-axis for combined vote diagram 24 ranges from −3 to +3. For example, at testing period 8, the combined vote is +3, thus prompting an adjustment of the target pressure level. Pressure diagram 23 illustrates the relative (cumulative) adjustments in target pressure level made by target pressure module 116 based on the combination of votes determined by voting module 115, per testing period. For testing periods with a large enough positive combined vote, the target pressure level may be decreased. For testing periods with a large enough negative combined vote, the target pressure may be increased.

Figure 3:
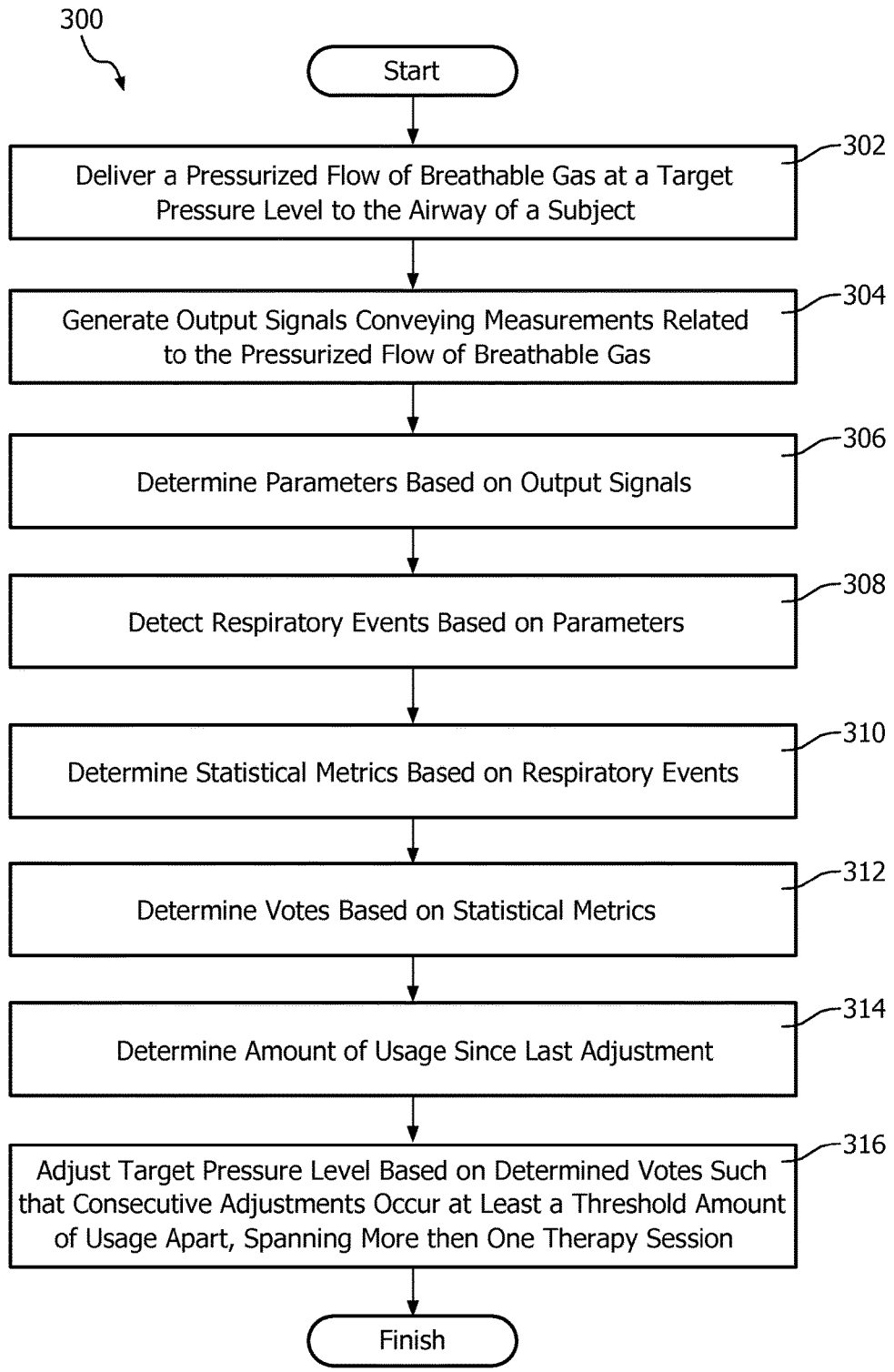
FIG. 3 illustrates a method for treating sleep apnea by adjusting a pressure level, according to certain embodiments.

FIG. 3 illustrates a method 300 for treating sleep apnea by adjusting a pressure level, according to certain embodiments. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow of breathable gas having a target pressure level is delivered to the airway of a subject. In one embodiment, operation 302 is performed by a pressure generator similar to or substantially the same as pressure generator 140 (shown in FIG. 1 and described above).

At an operation 304, output signals are generated conveying measurements related to the pressurized flow of breathable gas. In one embodiment, operation 304 is performed by a sensor similar to or substantially the same as sensor 142 (shown in FIG. 1 and described above).

At an operation 306, parameters are determined based on the generated output signals. The parameters may include gas parameters, breathing parameters, and/or other parameters. In one embodiment, operation 306 is performed by a parameter determination module similar to or substantially the same as parameter determination module 111 (shown in FIG. 1 and described above).

At an operation 308, respiratory events are detected based on the parameters and/or generated output signals. In one embodiment, operation 308 is performed by a respiratory event module similar to or substantially the same as respiratory event determination module 112 (shown in FIG. 1 and described above).

At an operation 310, statistical metrics are determined based on the respiratory events, parameters, and/or generated output signals. In one embodiment, operation 310 is performed by a statistical module similar to or substantially the same as statistical module 114 (shown in FIG. 1 and described above).

At an operation 312, votes are determined based on the statistical metrics, respiratory events, parameters, and/or generated output signals. In one embodiment, operation 312 is performed by a voting module similar to or substantially the same as voting module 115 (shown in FIG. 1 and described above).

At an operation 314, an amount of (therapeutic) usage since the preceding adjustment of the pressure level (or since initialization of the respiratory therapy device) is determined. In one embodiment, operation 314 is performed by a timing module similar to or substantially the same as timing module 113 (shown in FIG. 1 and described above).

At an operation 316, the target pressure level is adjusted based on detected respiratory events such that consecutive adjustments occur at least a threshold amount of usage apart, spanning more than one therapy session. In one embodiment, operation 316 is performed by a target pressure module similar to or substantially the same as target pressure module 116 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for treating sleep apnea of a subject having an airway by adjusting a pressure level, the system comprising:
   (a) a pressure generator configured to provide therapeutic usage by generating a pressurized flow of breathable gas for delivery to the airway of the subject, in accordance with a therapeutic regimen;
   (b) one or more sensors configured to generate output signals conveying measurements related to the pressurized flow of breathable gas and/or the airway of the subject; and
   (c) one or more processors operatively coupled with the one or more sensors and the pressure generator, and configured to execute computer program modules, the computer program modules comprising:
      a timing module configured to determine respiratory timing parameters based on the generated output signals;
      a respiratory event module configured to detect respiratory events based on the generated output signals and the respiratory timing parameters from the timing module;
      a statistic module configured to determine a measurement of variation of the detected respiratory events,
      a target pressure module configured to adjust a target pressure level based on the measurement of variation of the detected respiratory events, wherein the target pressure module is configured to adjust the target pressure level such that consecutive adjustments occur at least a threshold amount of therapeutic usage apart, wherein the threshold amount of therapeutic usage corresponds to therapeutic usage spanning more than one therapy session,
      a control module configured to control the pressure generator to adjust the pressurized flow of breathable gas such that the pressure at or near the airway of the subject is maintained at or near the target pressure level; and
      a voting module configured to:
         determine (i) a first vote indicating whether the subject is improving or declining responsive to detected respiratory events during a first set of therapy sessions being different from detected respiratory events during a second set of therapy sessions by more than a predetermined minimum measure of variation, wherein one or more therapy sessions of the second set precede the therapy sessions of the first set,
         determine (ii) a second vote indicating whether the subject is improving or declining responsive to detected respiratory events during the first set of therapy sessions being different from detected respiratory events during a third set of therapy sessions by more than the predetermined minimum measure of variation, wherein one or more therapy sessions of the third set precede the therapy sessions of the second set, and
         adjust a strength of the first vote and/or the second vote relative to each other based on an amount a difference in the detected respiratory events is more than the predetermined minimum measure of variation to indicate relatively large improvements or relatively large declines;
      wherein the target pressure module is configured such that adjusting the target pressure level based on the detected respiratory events comprises adjusting the target pressure level based on the votes determined by the voting module.

2. The system of claim 1,
   the respiratory timing parameters comprising:
      (i) one or more of (A) breathing period, (B) inhalation time or period, or (C) exhalation time or period; and
      (ii) one or more of (A) session length, or (B) average and/or cumulative daily and/or nightly usage.

3. The system of claim 1, wherein the voting module is further configured to determine a third vote indicating the subject is neither improving nor declining responsive to detected respiratory events during the first set of therapy sessions not being different from detected respiratory events during a second set and/or third set of therapy sessions by more than the predetermined minimum measure of variation.

4. The system of claim 1, wherein the second set of therapy sessions precedes the first set of therapy sessions, and wherein the third set of therapy sessions comprises the second set of therapy sessions.

5. The system of claim 1, wherein adjusting the target pressure level based on detected respiratory events is performed such that adjustments are made in between therapy sessions.

6. The system of claim 1, wherein the target pressure module configured to adjust a target pressure level based on the detected respiratory events is configured to decrease the target pressure level responsive to a determination that an index representing the detected respiratory events across a period spanning multiple therapy sessions has varied within a predetermined range of variability for the index.

7. The system of claim 1, wherein the predetermined minimum measure of variation is a standard deviation, wherein the first vote and/or the second vote indicate the subject is improving responsive to detected respiratory events during the first set of therapy sessions being less than a difference between detected respiratory events during the second set and/or third set of therapy sessions and the standard deviation, and wherein the first vote and/or the second vote indicate the subject is declining responsive to detected respiratory events during the first set of therapy sessions being greater than a sum of detected respiratory events during the second set and/or third set of therapy sessions and the standard deviation.

8. The system of claim 1, wherein the respiratory timing parameters comprise breathing period, inhalation time or period, exhalation time or period session length, and average and/or cumulative daily and/or nightly usage.

9. A method of treating sleep apnea of a subject having an airway by adjusting a pressure level, the method comprising;
   providing therapeutic usage by generating and delivering a pressurized flow of breathable gas having a pressure level at or near a target pressure level to the airway of a subject, in accordance with a therapeutic regimen;
   generating one or more output signals conveying measurements related to the pressurized flow of breathable gas and/or the airway of the subject;
   determining respiratory timing parameters based on the generated output signals;
   detecting respiratory events based on the generated output signals and the respiratory timing parameters;

determining a measurement of variation of the detected respiratory events;

adjusting the target pressure level based on the measurement of variation of the detected respiratory events, such that consecutive adjustments occur at least a threshold amount of therapeutic usage apart, wherein the threshold amount of therapeutic usage corresponds to therapeutic usage spanning more than one therapy session;

determining (i) a first vote indicating whether the subject is improving or declining responsive to detected respiratory events during a first set of therapy sessions being different from detected respiratory events during a second set of therapy sessions by more than a predetermined minimum measure of variation, wherein one or more therapy sessions of the second set precede the therapy sessions of the first set, and (ii) a second vote indicating whether the subject is improving or declining responsive to detected respiratory events during the first set of therapy sessions being different from detected respiratory events during a third set of therapy sessions by more than the predetermined minimum measure of variation, wherein one or more therapy sessions of the third set precede the therapy sessions of the second set; and adjusting a strength of the first vote and/or the second vote relative to each other based on an amount a difference in the detected respiratory events is more than the predetermined minimum measure of variation to indicate relatively large improvements or relatively large declines;

wherein adjusting the target pressure level based on the detected respiratory events comprises adjusting the target pressure level based on the first vote and the second vote.

10. The method of claim 9,
the respiratory timing parameters comprising:
(i) one or more of (A) breathing period, (B) inhalation time or period, or (C) exhalation time or period; and
(ii) one or more of (A) session length, or (B) average and/or cumulative daily and/or nightly usage.

11. The method of claim 9, further comprising: determining a third vote indicating the subject is neither improving nor declining responsive to detected respiratory events during the first set of therapy sessions not being different from detected respiratory events during a second set and/or third set of therapy sessions by more than the predetermined minimum measure of variation.

12. The method of claim 11, further comprising: determining a fourth vote based on a comparison of detected respiratory events during the first set of therapy sessions and detected respiratory events during a fourth set of therapy sessions, wherein one or more therapy sessions of the fourth set precede the therapy sessions of the first set, and wherein the therapy sessions of the fourth set span at least twice as much therapeutic usage as the therapy sessions of the first set.

13. The method of claim 9, wherein the second set of therapy sessions precedes the first set of therapy sessions, and wherein the third set of therapy sessions comprises the second set of therapy sessions.

14. The method of claim 9, wherein the adjustment of the target pressure level based on the measurement of variation of the detected respiratory events is made in between therapy sessions.

15. The method of claim 9, wherein the predetermined minimum measure of variation is a standard deviation, wherein the first vote and/or the second vote indicate the subject is improving responsive to detected respiratory events during the first set of therapy sessions being less than a difference between detected respiratory events during the second set and/or third set of therapy sessions and the standard deviation, and wherein the first vote and/or the second vote indicate the subject is declining responsive to detected respiratory events during the first set of therapy sessions being greater than a sum of detected respiratory events during the second set and/or third set of therapy sessions and the standard deviation.

16. The method of claim 9, wherein the respiratory timing parameters comprise breathing period, inhalation time or period, exhalation time or period session length, and average and/or cumulative daily and/or nightly usage.

17. A system configured to treat sleep apnea of a subject having an airway by adjusting a pressure level, the system comprising:

means for providing therapeutic usage by generating and delivering a pressurized flow of breathable gas having a pressure level at or near a target pressure level to the airway of a subject, in accordance with a therapeutic regimen;

means for generating one or more output signals conveying measurements related to the pressurized flow of breathable gas and/or the airway of the subject;

means for determining respiratory timing parameters based on the generated output signals;

means for detecting respiratory events based on the generated output signals and the respiratory timing parameters;

means for determining a measurement of variation of the detected respiratory events;

means for adjusting the target pressure level based on the measurement of variation of the detected respiratory events, such that consecutive adjustments occur at least a threshold amount of therapeutic usage apart, wherein the threshold amount of therapeutic usage corresponds to therapeutic usage spanning more than one therapy session;

means for determining (i) a first vote indicating whether the subject is improving or declining responsive to detected respiratory events during a first set of therapy sessions being different from detected respiratory events during a second set of therapy sessions by more than a predetermined minimum measure of variation, wherein one or more therapy sessions of the second set precede the therapy sessions of the first set, and (ii) a second vote indicating whether the subject is improving or declining responsive to detected respiratory events during the first set of therapy sessions being different from detected respiratory events during a third set of therapy sessions by more than the predetermined minimum measure of variation, wherein one or more therapy sessions of the third set precede the therapy sessions of the second set; and means for adjusting a strength of the first vote and/or the second vote relative to each other based on an amount a difference in the detected respiratory events is more than the predetermined minimum measure of variation to indicate relatively large improvements or relatively large declines; wherein the means for adjusting the target pressure level comprises means for adjusting the target pressure level based on the first vote and the second vote.

18. The system of claim 17,
the respiratory timing parameters comprising:
(i) one or more of (A) breathing period, (B) inhalation time or period, or (C) exhalation time or period; and
(ii) one or more of (A) session length, or (B) average and/or cumulative daily and/or nightly usage.

19. The system of claim 17, further comprising: means for deriving a third vote indicating the subject is neither improving nor declining responsive to detected respiratory events during the first set of therapy sessions not being different from detected respiratory events during a second set and/or third set of therapy sessions by more than the predetermined minimum measure of variation.

20. The system of claim 19, further comprising: means for deriving a fourth vote based on a comparison of detected respiratory events during the first set of therapy sessions and detected respiratory events during a fourth set of therapy sessions, wherein one or more therapy sessions of the fourth set precede the therapy sessions of the first set, and wherein the therapy sessions of the fourth set span at least twice as much therapeutic usage as the therapy sessions of the first set.

21. The system of claim 17, wherein the second set of therapy sessions precedes the first set of therapy sessions, and wherein the third set of therapy sessions comprises the second set of therapy sessions.

22. The system of claim 17, wherein the adjustment of the target pressure level based on the measurement of variation of the detected respiratory events is made in between therapy sessions.

23. The system of claim 17, wherein the predetermined minimum measure of variation is a standard deviation, wherein the first vote and/or the second vote indicate the subject is improving responsive to detected respiratory events during the first set of therapy sessions being less than a difference between detected respiratory events during the second set and/or third set of therapy sessions and the standard deviation, and wherein the first vote and/or the second vote indicate the subject is declining responsive to detected respiratory events during the first set of therapy sessions being greater than a sum of detected respiratory events during the second set and/or third set of therapy sessions and the standard deviation.

24. The system of claim 17, wherein the respiratory timing parameters comprise breathing period, inhalation time or period, exhalation time or period session length, and average and/or cumulative daily and/or nightly usage.

* * * * *